United States Patent [19]

Fraser et al.

[11] Patent Number: 4,730,625
[45] Date of Patent: Mar. 15, 1988

[54] POSTURE MONITORING SYSTEM

[75] Inventors: Gregory A. Fraser, Dollard des Ormeaux; Simon Raab, Lorraine, both of Canada

[73] Assignee: Faro Medical Technologies Inc., Montreal, Canada

[21] Appl. No.: 941,695

[22] Filed: Dec. 15, 1986

[51] Int. Cl.⁴ ............................................. A61B 5/10
[52] U.S. Cl. .................................. 128/781; 128/782; 128/905; 340/573
[58] Field of Search ............... 128/774, 781, 782, 905; 340/573; 446/26, 28; 73/159, 172, 862.45, 862.47, 862.48, 862.52, 862.62, 862.64, 862.65, 865.4

[56] References Cited

U.S. PATENT DOCUMENTS

| | | | |
|---|---|---|---|
| 3,305,036 | 2/1967 | Walters | 128/25 B |
| 3,504,540 | 4/1970 | Pradko et al. | 73/862.65 |
| 3,608,541 | 9/1971 | Hall | 340/573 |
| 3,791,375 | 2/1974 | Pfeiffer | 73/172 |
| 3,818,756 | 6/1974 | Barron et al. | 73/159 |
| 3,841,163 | 10/1974 | Daniel | 73/172 |

FOREIGN PATENT DOCUMENTS

83/02052  6/1983  PCT Int'l Appl. ................. 128/781

OTHER PUBLICATIONS

"Measuring Man's Stability of Stance", by Terekhov, Journal of Clinical Engineering, vol. 4, No. 1, Jan.-Mar. 1979, pp. 61 to 65.

Primary Examiner—Kyle L. Howell
Assistant Examiner—Randy Citrin
Attorney, Agent, or Firm—Fishman & Dionne

[57] ABSTRACT

An article of wearing apparel, to be worn on the upper body of a subject, includes a portion for covering the back of the subject. Sensors for sensing the changes in posture of the subject and providing electrical signals proportional to the degree of change in posture are removably mounted on the portion for covering the back of the subject. Electronic circuitry analyzes the electrical signals to provide an output, which can be sensed by the subject, when the posture of the subject deviates from a pre-set postural position by a predetermined amount. The electronic circuit is disposed in a carrier which is also removably mounted from the article of clothing apparel.

6 Claims, 4 Drawing Figures

U.S. Patent    Mar. 15, 1988    Sheet 1 of 2    4,730,625
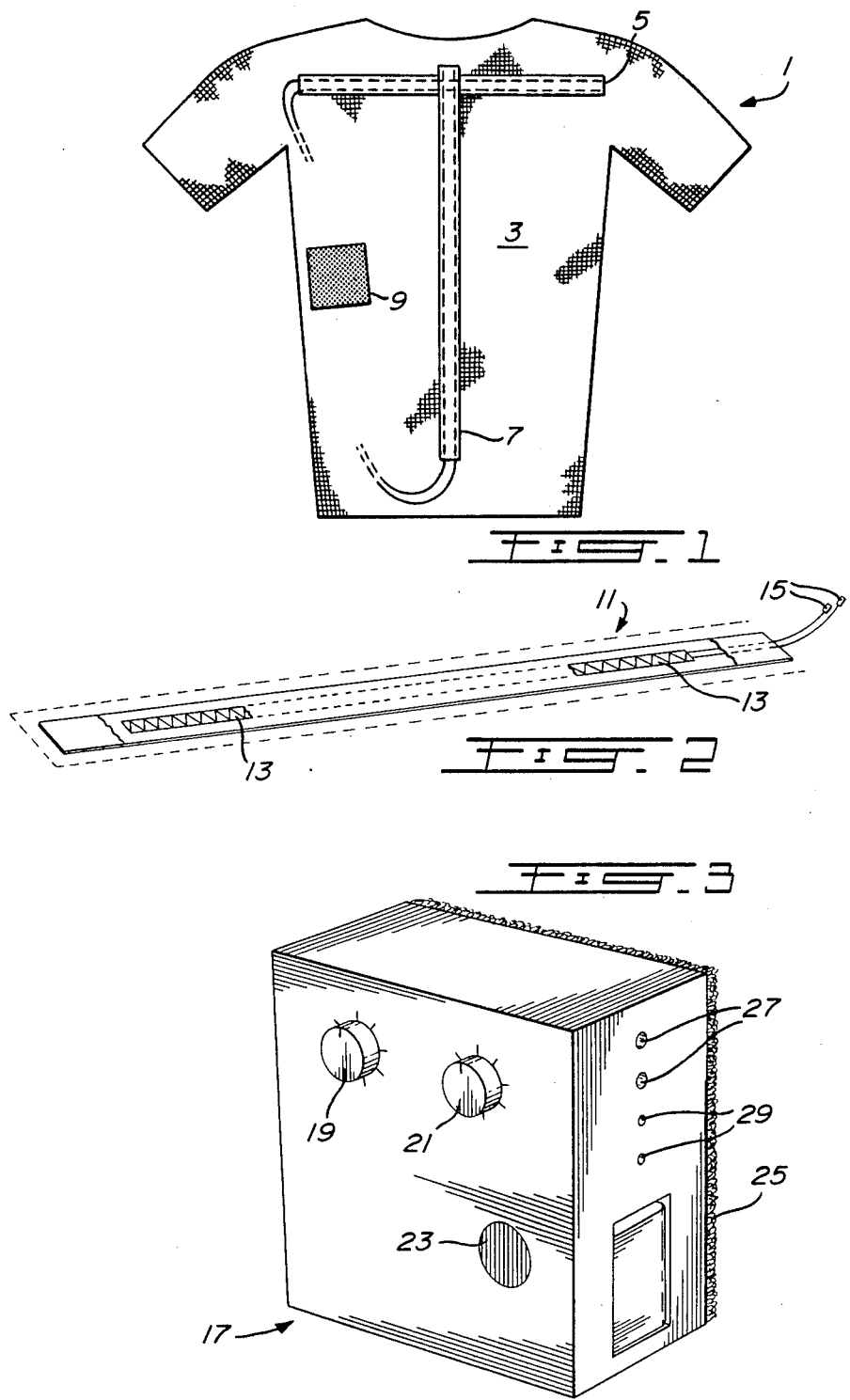

POSTURE MONITORING SYSTEM

BACKGROUND OF INVENTION

1. Field of the Invention

The invention relates to a posture monitoring system. More specifically, the invention relates to such a system which is removably mounted on wearing apparel of the subject whose posture is being monitored.

2. Description of Prior Art

Monitoring of posture is at times an element of the treatment of medical problems such as lower back pain. In order to be effective, posture monitoring systems should monitor the posture of the subject during all of his waking hours, and should provide a signal to the subject when his posture deviates by more than a predetermined amount.

"Measuring Man's Stability of Stance" by Terekhov, Journal of Clinical Engineering, Volume 4, No. 1, January-March 1979, pages 61 to 65, teaches a system for measuring stance in humans. However, the instrument is usable only in a static condition and therefore could not be used on a day long basis.

U.S. Pat. No. 3,818,756, Barron et al, June 25, 1974, teaches a system for measuring and indicating static and dynamic loads exerted upon different areas of a subject human body. It includes, for example, an article of wearing apparel, e.g., an undershirt, including a plurality of sensors mounted thereon. The sensors measure the pressure, exerted by an external force, on the human body. Accordingly, they could not measure changes in posture of the human body. In addition, although the individual sensors are removable, the strip for mounting the sensors is an integral part of the wearing apparel. Accordingly, the wearing apparel is not washable even when the sensors are removed.

U.S. Pat. No. 3,791,375, Pfeiffer, Feb. 12, 1974, teaches an audio signal source which is worn on the human body.

U.S. Pat. No. 3,305,036, Walters, Feb. 21, 1967, U.S. Pat. No. 3,841,163, Daniel, Oct. 15, 1974, and U.S. Pat. No. 3,504,540, Pradko et al, Apr. 7, 1970, all teach the use of strain gauges for measuring different human parameters.

SUMMARY OF INVENTION

It is an object of the invention to provide a posture monitoring system for monitoring the posture of a subject.

It is a more specific object of the invention to provide such a system which comprises an article of wearing apparel, and means for removably mounting posture sensors on said article of wearing apparel.

It is an even more specific object of the invention to provide such a system wherein said article of wearing apparel comprises an article of wearing apparel worn on the upper body of the subject, the sensors being removably mounted on a portion of the article of wearing apparel which covers the back of the subject.

In accordance with the invention there is provided a posture monitoring system for monitoring the posture of a subject. The system includes an article of wearing apparel to be worn on the upper body of the subject and including a portion for covering the back of the subject. Sensors are provided for sensing changes in postures of the subject, the sensors providing electrical signals corresponding to the changes in posture. Means are provided on the portion for removably mounting the sensors. Electronic means are provided for analyzing the electrical signals and for providing an output, which can be sensed by the subject, when the posture of the subject deviates from a pre-set position by a predetermined amount. Second means are provided for removably mounting the electronic means on the article of wearing apparel.

BRIEF DESCRIPTION OF DRAWINGS

The invention will be better understood by an examination of the following description, together with the accompanying drawings, in which:

FIG. 1 illustrates an article of wearing apparel in accordance with the invention;

FIG. 2 illustrates a posture sensor in accordance with the invention;

FIG. 3 illustrates a carrier for the electronics means; and

DESCRIPTION OF PREFERRED EMBODIMENTS

Figure 4:
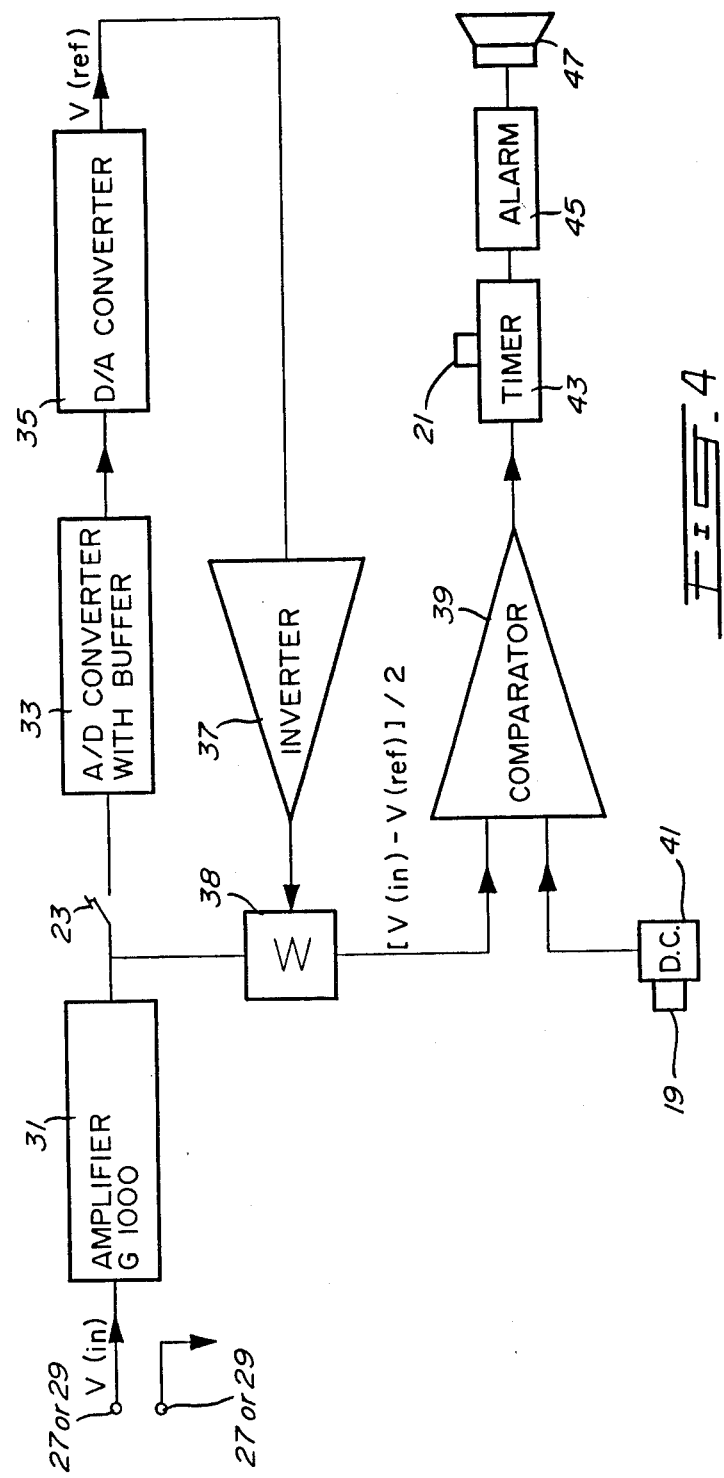
FIG. 4 illustrates a schematic circuit of the electronics means.

Referring to FIG. 1, the article of wearing apparel 1 comprises, in accordance with the invention, a T-shirt or undershirt worn on the upper body of a subject. The shirt should be snug-fitting and is therefore made of a stretchable material as is well known in the art.

The shirt includes a portion 3 which covers the back of the subject. Disposed on the portion 3 are means for removably mounting sensors illustrated in FIG. 1 as horizontal pocket 5 and vertical pocket 7. A second mounting means 9, comprising in the illustrated embodiment a Velcro TM pad, is provided for the mounting of the electronic box to be described below.

Referring to FIG. 2, the posture sensor 11 comprises an elongated strip, which would fit into either pocket 5 or 7, and comprising strain gauges, preferably, semiconductor strain gauges 13. As is well known in the art, when a strain is applied to such strain gauges, they will produce at their output, conductors 15, an electrical signal which is proportional to the amount of strain applied. Thus, when a subject bends out of normal posture, he will apply a strain to the strain gauges. The electrical signal thus produced will be a function of the degree that the subject has bent away from the normal posture.

A carrier for electronics means, illustrated at 17 in FIG. 3, includes a sensitivity control 19 and a timer control 21. In accordance with the illustrated embodiment, these constitute rotary controls for controlling the magnitude of, for example, a variable resistor. The box 17 also includes a push-to-set button 23 whose function will be described below.

A Velcro TM pad 25 is mounted on the back of the box for engagement with the Velcro TM pad 9 on the T-shirt 1.

Conductors 15 of the sensors 11 are applied to terminals 27 or 29 respectively.

The electronic means comprise electronic circuit for analyzing the output of the sensors as illustrated in FIG. 4. Referring to FIG. 4, the output of a respective sensor is first applied to an amplifier 31 to amplify the signal. The output of amplifier 31 is applied, on one path, to an analog-to-digital converter with buffer 33 through switch 23. The output of 33 is applied to a digital-to-analog converter whose output is applied to inverter 37.

In a second path, the output of amplifier 31 is applied to one input terminal of a summer 38 whose other input terminal is fed from the inverter 37. The output of the summer 38 is fed to one input terminal of a comparator 39 whose other input is fed from a DC source 41. The output of the comparator is fed to a timer 43 whose output is in turn fed to an alarm 45. The output of the alarm 45 is fed to a speaker 47.

In operation, the system works as follows:

Sensors are disposed in the pockets 5 and 7, and the subject puts on the shirt 1 so that the portion 3 covers his back. Conductors 15 of the respective sensors are connected to terminal sets 27 or 29 of the electronics carrier 17 which has been mounted on the velcro pad 9.

In order to set a reference level, the subject then stands up straight, for example, against a straight wall, and depresses the button 23. With button 23 applied, the input signal, after amplification in amplifier 31 (the reference signal), is applied to the analog-to-digital converter 33 where it is converted to a digital value and stored in the buffer in 33. The output of the analog-to-digital converter 33 continuously drives the digital-to-analog converter 35 so that the output of 35 is equal in magnitude and sense (i.e. positive or negative) to the reference signal. The output of 35 is then applied to the input of inverter 37 so that the output of 37 is equal in magnitude but opposite in sense to the reference signal.

The push button switch 23 is then released so that the input signal is no longer applied to analog-to-digital converter 33. However, because the initial reference level is stored in the buffer of 33, it continues to be available for reference throughout the remainder of the monitoring period.

The subject then continues in his normal movements throughout the monitoring period. Each time that he bends out of straight posture, he applies a strain to the strain gauges which causes an electrical signal to be produced at either terminals 27 or 29. This signal is summed with the inverse of the reference signal in the summer 38, and the sum is then applied to one input terminal of the comparator 39. The sensitivity level of the system is set by the DC level of the DC source 41. For example, if the system is to be very sensitive, then the output of 41 will be a very small DC level so that even minute deviations from a straight posture will produce a warning signal. If the output of 41 is made large, then only large deviations from a straight posture will produce a warning signal.

When the output of the summer 38 is greater than the level of 41, then the output of comparator 31 will trigger the timer 43. The output of the timer 43 will trigger alarm 45 after a pre-set time is exceeded.

As it is the purpose of the system to monitor long term posture deviations from norm, it would not be desirable to trigger an alarm each time there is a spontaneous short-term movement out of postural alignment. Thus, the timer ensures that only long-term deviations will trigger an alarm.

When the alarm is triggered, it will drive the speaker 47 to produce an audible tone. The subject is then alerted to return to his proper posture.

In view of the fact that the sensors are removably mounted from the T-shirt, and the electronics carrier is similarly removably mounted, the T-shirt is washable when the sensors and the electronics are removed. It will be understood that although pockets were illustrated for the purpose of removably mounting the sensors in FIG. 1, other means, for example, Velcro TM strips, could be used for this purpose. In the same way, the electronics could be mounted in a pocket instead of on a Velcro TM pad. Zippered arrangements or buttoned arrangements, as well known in the art, could also be used for these purposes.

Although an audible signal producer 47 has been illustrated, other signals which can be sensed by the subject could also be used. For example, a conductor could be connected to the subject's skin to provide a mild shock when the posture deviates too great an amount. Alternatively, a tactile sensation could be provided by a vibrator mounted on the skin of the user.

Although discrete electronic elements have been illustrated for the purpose of electronic analysis, it will of course be appreciated that these functions could be performed by a microprocessor appropriately programmed, and such an embodiment is also considered to be a part of the present invention.

In setting the level, the subject will align his back against the wall ensuring a gap of no more than one hand's thickness at the region of the lumbar spine and neck. When this posture is obtained, button 23 would be pressed.

In order to set the sensitivity, the subject is bent to the smallest deviation for producing an alarm. Knob 19 would then be rotated until an alarm signal is just produced in this postural position.

The timer is adjusted to produce an alarm signal with the subject in the smallest deviation after a predetermined period.

Although particular embodiments have been described, this was for the purpose of illustrating, but not limiting, the invention. Various modifications, which will come readily to the mind of one skilled in the art, are within the scope of the invention as defined in the appended claims.

We claim:

1. A posture monitoring system for monitoring the posture of a subject, comprising:
   an article of wearing apparel to be worn on the upper body of the subject including a portion for covering the back of the subject;
   a plurality of sensor means for sensing changes in posture of said subject, said sensor means including means for providing electrical signals proportional to the degree of change in posture;
   first means on said portion for removably mounting said sensor means;
   electronic means for analyzing said electrical signals and for providing an output, which can be sensed by said subject, when the posture of the subject deviates from a pre-set postural position by a predetermined amount; and
   second means for removably mounting said electronic means on said article of wearing apparel.

2. A system as defined in claim 1 and comprising two sensors;
   said first means comprising a first pocket, extending in a vertical direction, for removably mounting one of said sensor means; and
   said first means further comprising a second pocket, extending in a horizontal direction, for removably mounting the other of said sensors.

3. A system as defined in claim 2 wherein said electronic means is disposed in a carrier;
   said second means for removably mounting comprising a Velcro TM pad mounted on said article of wearing apparel;

a second Velcro ™ pad mounted on said carrier for engaging with said Velcro ™ pad on said article of wearing apparel.

4. A system as defined in claim 3 wherein said electronic means comprises an electronic circuit including:

means for storing a reference electrical signal level indicative of a straight posture;

means for comparing said reference signal with said electrical signals and providing a different signal indicative of the difference between said reference signal and said electrical signals; and alarm means for generating an alarm when said different signal exceeds a predetermined level.

5. A system as defined in claim 4 wherein said electronic means comprises sensitivity setting means.

6. A system as defined in claim 5 wherein said electronic means comprises means for setting said reference electrical signal.

* * * * *